United States Patent [19]

Böhme

[11] 4,138,397

[45] Feb. 6, 1979

[54] 6-(2,3-DIHYDRO-5-BENZOFURANYL)-ACETAMIDO PENICILLIN DERIVATIVES

[75] Inventor: Ekkehard H. Böhme, Cincinnati, Ohio

[73] Assignee: Richardson-Merrell Inc., Wilton, Conn.

[21] Appl. No.: 881,610

[22] Filed: Feb. 27, 1978

[51] Int. Cl.$^2$ ............... C07D 499/68; C07D 499/58; C07D 499/60; C07D 499/62

[52] U.S. Cl. .................................. 260/239.1; 424/271

[58] Field of Search ................................ 260/239.1

[56] References Cited

U.S. PATENT DOCUMENTS 3,994,876  11/1976  Erickson et al. .................. 260/239.1

Primary Examiner—Gerald A. Schwartz
Attorney, Agent, or Firm—L. Ruth Hattan; Eugene O. Retter; George W. Rauchfuss, Jr.

[57] ABSTRACT

New 6-(2,3-dihydro-5-benzofuranyl)acetamido penicillin compounds are described which are useful as antibacterial agents.

12 Claims, No Drawings

6-(2,3-DIHYDRO-5-BENZOFURANYL-)ACETAMIDO PENICILLIN DERIVATIVES

BACKGROUND OF THE INVENTION

Field of Invention

This invention is directed to new penicillin derivatives which are useful as antibiotics and methods of preparing same.

SUMMARY OF THE INVENTION

Compounds of formula 1 are useful as antibiotics wherein

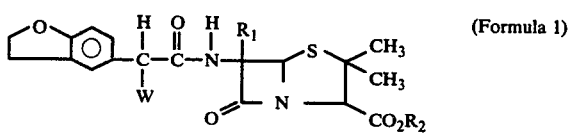

(Formula 1)

W is hydrogen, $-NHR_3$, $-OH$, $-CO_2R_4$ or $-SO_3R_4$. $R_3$ is hydrogen, a straight or branched 2 to 5 carbon alkanoyl group, or an alkoxycarbonyl group in which the alkoxy group is straight or branched and contains 1 to 4 carbon atoms, $R_4$ is hydrogen or a straight or branched 1 to 4 carbon alkyl group. $R_1$ is hydrogen or methoxy. $R_2$ is hydrogen, a straight or branched alkyl group of from 1 to 4 carbon atoms, an alkanoyloxymethyl group in which the alkanoyl moiety is straight or branched and has from 2 to 5 carbon atoms and the amino nitrogen may be substituted with a straight or branched alkyl group of from 1 to 4 carbon atoms, an alkoxycarbonylaminomethyl group wherein the alkoxy moiety is straight or branched and has from 1 to 4 carbon atoms and the amino nitrogen may be substituted with a straight or branched alkyl group of from 1 to 4 carbon atoms, a p-(alkanoyloxy)benzyl group in which the alkanoyl moiety has from 2 to 5 carbon atoms and is straight or branched, or an aminoalkanoyloxymethyl group wherein the alkanoyl moiety is straight or branched and contains from 2 to 15 carbon atoms and the amino nitrogen may be mono- or disubstituted with a straight or branched alkyl group of from 1 to 4 carbon atoms; and nontoxic pharmaceutically acceptable salts and individual optical isomers thereof.

DETAILED DESCRIPTION OF THE INVENTION

In formula 1 the substituent group represented by $R_2$ is hydrogen.

In addition to the above, $R_2$ is a straight or branched alkyl group of from 1 to 4 carbon atoms. Or $R_2$ may be an alkanoyloxymethyl group represented by the formula

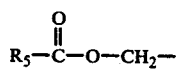

wherein $R_5$ is a straight or branched alkyl group of from 1 to 4 carbon atoms. Additionally, $R_2$ may be an alkanoylaminomethyl or an alkoxycarbonylaminomethyl group represented by

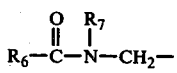

wherein $R_6$ is a straight or branched alkyl group of from 1 to 4 carbon atoms or a straight or branched alkoxy group of from 1 to 4 carbon atoms and $R_7$ is hydrogen or a straight or branched alkyl group of from 1 to 4 carbon atoms. $R_2$ may be an alkanoyloxybenzyl group represented by the formula

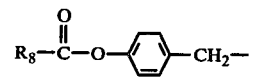

wherein $R_8$ is a straight or branched alkyl group of from 1 to 4 carbon atoms. $R_2$ may be an aminoalkanoyloxymethyl group represented by the formula

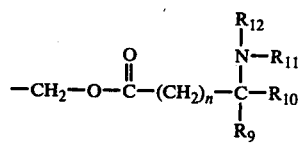

wherein n is 0 to 5, and each of $R_9$ and $R_{10}$ is selected from hydrogen or a straight or branched alkyl group of from 1 to 4 carbon atoms and each of $R_{11}$ and $R_{12}$ is selected from hydrogen or a straight or branched alkyl group of from 1 to 4 carbon atoms.

Illustrative examples of the straight or branched alkyl groups of from 1 to 4 carbon atoms which $R_2$ and $R_5$ to $R_{12}$, inclusive, may represent are: methyl, ethyl, n-propyl, isopropyl, n-butyl, isobutyl and tert-butyl.

Illustrative examples of the straight or branched alkoxy groups of from 1 to 4 carbon atoms which $R_6$ may represent are: methoxy, ethoxy, n-propoxy, isopropoxy, n-butoxy, sec-butoxy and tert-butoxy.

In formula 1, the substituent group $R_1$ is hydrogen or methoxy.

Illustrative examples of the alkanoyl groups represented by $R_2$ are the following: acetyl, propionyl and butyryl.

In the formula 1, W is hydrogen or hydroxyl or W is $-NHR_3$ wherein $R_3$ is hydrogen, a straight or branched 2 to 5 carbon alkanoyl group or an alkoxycarbonyl group in which the alkoxy moiety is straight or branched and has from 1 to 4 carbon atoms.

Additionally, W is a $-COOR_4$ or an $-SO_3R_4$ group wherein $R_4$ is hydrogen. $R_4$ is also a straight or branched alkyl group of from 1 to 4 carbon atoms.

Illustrative examples of alkyl groups as represented by $R_4$ are: methyl, ethyl, n-propyl, isopropyl, n-butyl and tert-butyl.

It is apparent that $R_1$ exhibits either a cis or a trans spatial relationship with the hydrogen at position 5 in formula 1. The cis and trans isomers are within the scope of the invention; the compounds with the cis configuration being preferred.

The optical isomers of the compounds represented by formula 1 are also within the scope of this invention.

The non-toxic pharmaceutically acceptable acid addition salts of reaction of compounds of formula 1 with nontoxic pharmaceutically acceptable mineral acids, for example, hydrogen chloride, hydrogen bromide, hydrogen iodide, sulfate, sulfonate and phosphate and organic acid, for example, maleate, acetate, citrate, oxalate, succinate, benzoate, tartrate, fumarate, malate, mandelate and ascorbate forms the non-toxic pharmaceutically acceptable salts thereof which are included within the scope of this invention.

Also within the scope of this invention are the nontoxic pharmaceutically acceptable salts of compounds of formula 1 wherein W represents —$CO_2R_4$ or —$SO_3R_4$ ($R_4$=H) and $R_2$ is hydrogen formed by reacting an acid with a base, for example, primary, secondary and tertiary amines such as cyclohexylamine, dibutylamine, trioctylamine, procaine and dibenzylamine and the alkali metal and alkaline earth metal compounds such as sodium hydroxide, potassium carbonate, magnesium hydroxide and calcium oxide.

The compounds of this invention may be administered in a manner similar to that of many well known penicillin derivatives such as ampicillin, penicillin G, N and V. They may be administered orally or parenterally to warm blooded animals, that is, birds and mammals, for example, cats, dogs, cows, sheep, horses and humans. For oral administration the compounds may be administered in the form of tablets, capsules or pills or in the form of elixirs or suspensions. For parenteral administration they may be used in the form of sterile aqueous solutions which may contain other solutes, for example, enough saline or glucose to make the solutions isotonic.

Illustrative examples of bacteria against which the compounds of this invention are active are Staphylococcus aureus, Streptococcus pyogenes and Diplococcus pneumoniae.

An illustrative example of a compound of this invention is 6[[α-amino(2,3-dihydro-5-benzofuranyl)acetyl]amino]-3,3-dimethyl-7-oxo-4-thia-1-azabicyclo[3.2.0-]heptane-2-carboxylic acid.

Compounds of formula 1 are prepared by coupling a compound of formula 2

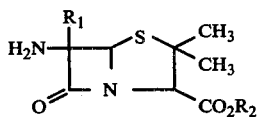

Formula 2 with a compound of formula 3

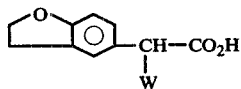

Formula 3 or functional equivalents thereof wherein $R_1$, $R_2$ and W have the meanings defined for formula 1. It is provided that when W is —$NHR_3$ ($R_3$=H) or —OH, these groups represented by W must be protected during the coupling reaction. When W is $CO_2R_4$ or $SO_3R_4$ ($R_4$=H), these groups represented by W may be protected during the coupling reaction. Optionally, the coupling reaction may be run in the presence of a dehydrating agent such as a carbodiimide such as dicyclohexylcarbodiimide. After the coupling reaction is completed, the protecting groups may be removed. For example, acid hydrolysis as illustrated in *Chem. Ber.*, 98, 789 (1965) or hydrogenolysis as illustrated in *J. Chem. Soc.*, 1440 (1962) may be used to remove the protecting groups.

Illustrative examples of protecting groups which are used for the specific reactive groups such as —$NHR_3$, —OH, —$CO_2R_4$ and —$SO_3R_4$ wherein $R_3$ and $R_4$ are as follows. For an amine group the protecting group may be an alkoxycarbonyl group, for example, tert-butoxycarbonyl; an alkanoyl group for example, an acetyl group, a [3-ethoxy-1-methoyl-3-oxo-1-propen-1-yl] group or a benzyloxycarbonyl group. The hydroxyl group may be protected with, for example, a trimethylsilyl group. Acid groups such as —$CO_2H$ and —$SO_3H$ may be protected with an alkyl group, such as, methyl, ethyl or tert-butyl.

The amino acids of compounds of Formula 3, W is —$NHR_3$, $R_3$ is hydrogen, may be protected for the coupling reaction by reacting the amino acid in a suitable solvent such as ethyl ether, tetrahydrofuran or methylene chloride containing an acid acceptor such as triethylamine with 1 equivalent of an alkanoyl halide such as acetyl chloride or butyryl bromide at 0° to 35° C. for from 0.5 hour to 2 hours. Or the amino acid of formula 3, W is —$NHR_3$, $R_3$ is hydrogen, may be reacted with an equivalent amount of an alkoxycarbonylazide such as ethoxycarbonylazide or isobutyrylcarbonylazide in a suitable solvent such as tetrahydrofuran, ethyl ether or methylene chloride which contains a basic material such as triethylamine or an alkaline bicarbonate. The reaction is run at from 0° to 40° C. for from 4 to 24 hours. Reaction of the amino acid of formula 3, 1 equivalent, W is —$NHR_3$, $R_3$ is hydrogen, with 1.05 equivalents of ethyl acetoacetate in methanolic potassium hydroxide at reflux for 5 to 30 minutes gives the corresponding amino acid protected with a [3-ethoxy-1-methyl-3-oxo-1-propen-1-yl] group. Or the amino group in the amino acid of Formula 3 may be protected by reacting the amino acid with benzyl chloroformate in aqueous solution at 0° C. for about 60 minutes, the pH of the solution being maintained at 8 to 9 by the use of sodium hydroxide.

The hydroxyl group is protected by reacting the appropriate acid as represented by formula 3, W is hydroxyl, with a slight excess of bis-(trimethylsilyl)acetamide in THF at reflux. An acid of formula 3 with a trimethylsilated hydroxyl group is obtained. The esters of the acids of formula 3 may be prepared by reacting the acids with thionyl chloride in THF, methylene chloride or ethyl ether containing dimethylformamide at room temperature to 40° C. for from 2 hours to 50 hours. When W is —$CO_2R_4$, $R_4$ is hydrogen, the acid of formula 3 is reacted with 1 equivalent of thionyl chloride, $PCl_5$ or $POCl_3$ to form the monoacid halide which is converted to the monoester by reaction with a low molecular weight alcohol. When W is —$SO_3R_4$, $R_4$ is hydrogen, the acid is reacted with 2.5 to 4 equivalents of thionyl chloride, $PCl_5$ or $POCl_3$ to form the diacid chloride. The resulting diacid chloride is reacted with 1 equivalent of water to give the corresponding chlorosulfonyl acetic acid derivative which is converted to the sulfonate ester of the acetic acid derivative by reaction with a low molecular weight alcohol such as methanol, ethanol, propanol or butanol.

Functional equivalents of the acid as represented by compounds of formula 3 include the acid halide such as the acid chloride, acid anhydrides, including mixed anhydrieds, with for example, alkylphosphoric acids, lower aliphatic monoesters of carbonic acid or alkyl or aryl sulfonic acids.

The coupling reaction is generally carried out in the presence of a solvent. Suitable solvents include ethyl acetate, chloroform, acetone, dioxane, tetrahydrofuran (THF), dimethylformamide (DMF), ether, ethanol, benzene and ethanol-benzene. As hydrophilic solvents are employed, mixtures of these solvents with water are also suitable for the above reactions. The coupling reaction is generally carried out in the presence of an acid acceptor (a base), for example, triethylamine or an alkaline bicarbonate. The temperature of the reaction may vary from −10° C. to 100° C., and the reaction time may vary from about ½ hour to 10 hours. The penicillin products are isolated by conventional means.

The acids as represented by compounds of formula 3 are coupled as the (D), the (L) or mixtures of the (D) and (L) optical isomers when W is other than hydrogen or —$CO_2R_4$. When W is hydrogen or —$CO_2R_4$, no optical activity is present and these compounds are coupled as described above.

For example, an acid as represented by formula 3 may be coupled to a compound as represented by formula 2 using the general procedure described in *J. Med. Chem.*, 9, 746 (1966) with the proviso that when W is other than hydrogen, these groups such as —$NHR_3$, —OH, —$CO_2R_4$ and —$SO_3R_4$, $R_3=R_4=H$, are protected. The acid to be coupled is reacted with a slight excess (1.05 equivalents) of an alkylchloroformate such as isobutylchloroformate at about −10° C. in a solvent which contains an acid acceptor such as triethylamine or sodium bicarbonate. After reaction is complete, 1 equivalent of a compound represented by formula 2 is added, the temperature is raised from −10° C. to about 20° C. and the reaction completed after 2-3 hours. The coupled product is recovered by known means.

Illustratively, an acid as represented by compounds of formula 3 wherein W is H, —OH, —$NHR_3$, —$CO_2R_4$ and —$SO_3R_4$ ($R_3=R_4=H$) may be coupled to an amine as represented by a compound of formula 2 in a suitable solvent such as tetrahydrofuran, chloroform or dioxane by the use of a carbodiimide, for example, N,N'-dicyclohexylcarbodiimide at a temperature of from −10° to 40° C. for from 2 to 18 hours by the general procedure as taught in U.S. Pat. No. 3,252,973, with the proviso that when W is other than H and $R_3=R_4=H$, the groups represented by W are protected.

Illustratively, an acid as represented by compounds of formula 3 may be converted to an acid halide by reaction with thionyl chloride, $PBr_5$, $POCl_3$ in a solvent such as ethyl ether, methylene chloride or chloroform at 10° to 60° C. for from 1 to 6 hours. The active groups such as —$NHR_3$, —OH, —$CO_2R_4$ or —$SO_3R_4$, $R_3=R_4=H$, may be protected prior to formation of the acid halide when present as part of the compound of formula 3. The acid halide may be reacted with an amine as represented by formula 2 in a suitable solvent which generally contains an acid acceptor such as triethylamine or an alkaline bicarbonate at a temperature of from 10° to 50° C. for from 1 to 12 hours.

Optionally, the groups used to protect the amine group in compounds represented by formula 1 may be removed by means of acid hydrolysis during work-up or by means of hydrogenolysis as described in *Chem. Ber.*, 98, 789 (1965) and *J. Chem. Soc.*, 1440 (1962) respectively.

For example, compounds of formula 1 which contain an amino group protected with a [3-ethoxy-1-methyl-3-oxo-1-propen-1-yl] group may be deprotected by subjecting the protected compound to an aqueous medium, for example, water, methanol, ethanol, propanol, tetrahydrofuran or mixtures thereof maintained at a pH of from 1 to 3 for 5 to 30 minutes at from 10° to 30° C. Additionally, compounds of formula 1 which contain an amine group protected with a benzyloxycarbonyl group may be deprotected by subjecting the protected compound to hydrogen gas at a pressure of 10 to 60 pounds/in² in a low molecular weight alcohol such as methanol, ethanol or propanol in the presence of a catalyst such as palladium on carbon for from 30 minutes to 8 hours at a temperature of 15° to 60° C.

Treatment of compounds of formula 1 wherein W is a hydroxyl group protected with a trimethylsilyl group, in a solvent such as water, methanol, ethanol, propanol, tetrahydrofuran or mixtures thereof maintained at a pH of from 1 to 3 for from 5 to 30 minutes at 10° to 30° C. gives the unprotected compound.

Compounds of formula 2 wherein $R_1$ is hydrogen and $R_2$ is hydrogen are commercially available or may be prepared by methods well known in the art. Compounds of formula 2 wherein $R_1$ is methoxy and $R_2$ is hydrogen are prepared according to the general procedures described in U.S. Pat. No. 3,778,432.

Compounds of formulas 1 and 2 wherein $R_2$ is alkanoyloxymethyl may be prepared by reacting the corresponding acid, $R_2$ is hydrogen, in the form of a salt, such as an alkali metal salt or the triethylammonium salt with an equivalent of a compound of the formula:

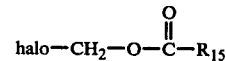

wherein halo is chlorine or bromine, $R_{15}$ is a straight or branched alkyl group of from 1 to 4 carbon atoms, by the general procedure described in U.S. Pat. No. 3,655,658.

Compounds of formulas 1 and 2 wherein $R_2$ is alkanoylaminomethyl or alkoxycarbonylaminomethyl are prepared by treating a salt such as the alkali metal salt or the trimethylammonium salt, of the corresponding acid, $R_2$=hydrogen, derivative of formulas 1 and 2 in an organic solvent such as dimethylformamide or hexamethylphosphoramide at 10° to 30° C. with an equivalent amount of an alkanoylaminomethyl halide or an alkoxycarbonylaminomethyl halide for ½ to 3 hours after which the mixture is poured into ice water. The resulting precipitated product is isolated by standard procedures.

Compounds of formulas 1 and 2 wherein $R_2$ is p-(alkanoyloxy)benzyl are prepared by adding 2 equivalents of the p-(alkanoyloxy)benzyl alcohol to an equivalent of the salt, for example, the alkali metal salt or the triethylammonium salt of the corresponding acid derivative, $R_2$=hydrogen, of formulas 1 and 2 and dimethylformamide or hexamethylphosphoramide after which the mixture is cooled to 0° C. One to 2 equivalents of dicyclohexylcarbodiimide and dimethylformamide are added dropwise to the mixture with stirring. The mixture is stirred at 0° C. for ½ to 3 hours and then an additional 2 to 5 hours at room temperature. The formed dicyclohexylurea is removed by filtration. The filtration is diluted with chloroform, methylene chloride or ethyl acetate, washed with water, dried and evaporated to give the product.

Compounds of formulas 1 and 2 wherein $R_2$ is aminoalkanoyloxymethyl are prepared by mixing a suspension of the salt, for example, the alkali metal salt or the triethylammonium salt of the corresponding acid, $R_2$=hydrogen, of formulas 1 and 2 and an excess of an appropriate amine protected aminoalkanoyloxymethyl halide in a solvent such as dimethylformamide, hexamethylphosphoramide or dimethylsulfoxide for 2 to 96 hours at 10° to 30° C. The mixture is then diluted with a solvent such as ethyl acetate or methylene chloride, washed with water, aqueous base, then water. The organic phase is separated and the precipitate isolated by conventional means followed by deprotection of the amine group to give the product.

The compound of formula 3 wherein W is an amine group is prepared by a modification of the method described in *Tetrahedron*, 31, 863 (1975).

For example, equivalent amounts of α-hydroxyhippuric acid and 2,3-dihydrobenzofuran in a suitable solvent such as 5% to 50% sulfuric acid-95% to 50% acetic acid mixture, or from 50% to 100% sulfuric acid are reacted at from 0° to about 25° C. for from 1 to 72 hours. α-Benzamido(2,3-dihydro-5-benzofuranyl)acetic acid is recovered from the reaction mixture.

α-Amino(2,3-dihydro-5-benzofuranyl)acetic acid may be recovered from the corresponding α-benzamido derivative which is dissolved in a low molecular weight alcohol such as methanol, ethanol, isopropanol or butanol and subjected to hydrogen gas at a pressure of from 10 to 70 pounds/in$^2$ in the presence of a suitable catalyst such as palladium on carbon or palladium on barium sulfate for from 1 to 8 hours at a temperature of from 20° to 50° C. or by treating said α-benzamido derivative in a low molecular weight alcohol such as methanol, ethanol or butanol or water containing a suitable mineral acid such as sulfuric, hydrochloric, hydrobromic or phosphoric acid for from 1 to 8 hours at a temperature of from about 30° to 110° C. and treating the thus formed acid salt with a base such as triethylamine, sodium hydroxide, potassium bicarbonate, sodium bicarbonate or a basic ion exchange resin such as Amberlite IR45 ® to form α-amino(2,3-dihydro-5-benzofuranyl)acetic acid.

Compounds of formula 3 wherein W is —NHR$_3$ and R$_3$ is a 2 to 5 alkanoyl group or an alkoxycarbonyl group wherein the alkoxy group contains 1 to 4 carbon atoms may be prepared by the following procedures. An amine compound represented by formula 3 wherein W is —NHR$_3$ and R$_3$ is hydrogen is reacted in a suitable solvent such as ethyl ether, tetrahydrofuran, methylene chloride, chloroform or benzene with a 2 to 5 carbon acid halide, wherein the halide is chlorine or bromine, for example, acetyl chloride, propionyl chloride or butyryl bromide at 0° to 50° C. for from 1 to 24 hours optionally in the presence of a basic material such as triethylamine, sodium bicarbonate or sodium carbonate to give a compound of formula 3 wherein R$_4$ is a 2 to 5 carbon alkanoyl group.

An amine compound represented by formula 3 wherein W is —NHR$_3$ and R$_3$ is hydrogen may be reacted with an alkoxycarbonylazide wherein the alkoxy group is from 1 to 4 carbon atoms, for example, ethoxycarbonylazide, propoxycarbonylazide or isobutoxycarbonylazide, in a suitable solvent such as ethyl ether, tetrahydrofuran, methylene chloride, chloroform or benzene optionally in the presence of basic material such as triethylamine, sodium bicarbonate or sodium carbonate at a temperature of from 0° to 50° C. for from 1 to 24 hours to produce a compound of formula 3 wherein W is —NHR$_3$ and R$_3$ is a 1 to 4 carbon alkoxycarbonyl group.

The compound of formula 3 wherein W is a hydroxyl group may be prepared from the corresponding amine compound of formula 3, W is —NHR$_3$ and R$_3$ is hydrogen. One equivalent of α-amino(2,3-dihydro-5-benzofuranyl)acetic acid in a suitable acid such as hydrochloric, hydrobromic, sulfuric, phosphoric or acetic acid is reacted with 1 to 3 equivalents of an alkali metal nitrite such as sodium nitrite or potassium nitrite at a temperature of from 30° to 70° C. for from 2 to 8 hours to give the desired α-hydroxy(2,3-dihydro-5-benzofuranyl)acetic acid.

The compound of formula 3 wherein W is hydrogen is prepared from the thus produced α-hydroxyacetic acid derivative. The compound of formula 3 wherein W is hydroxyl is added to a low molecular weight alcohol such as methanol, ethanol, propanol or butanol which contains a suitable acid catalyst such as sulfuric, phosphoric, hydrochloric, or hydrobromic and is refluxed for from 1 to 6 hours and the α-hydroxy ester corresponding to the low molecular weight alcohol used is then recovered. The thus formed α-hydroxy ester may be reacted with either an acid anhydride such as acetic anhydride, propionic anhydride and butanoic anhydride or an alkanoyl halide such as acetyl chloride, propionyl bromide or butyryl chloride in a suitable solvent such as ethyl ether, tetrahydrofuran, methylene chloride or n-propyl ether at a temperature of from 10° C. to the reflux temperature of the solvent used for from 1 to 6 hours. The alkanoyloxy ester derivative recovered is added to a low molecular weight alcohol such as methanol, ethanol, propanol or butanol and is treated with hydrogen gas at a pressure of 20 to 60 pounds/in$^2$ at 10° to 30° C. for from 1 to 4 hours in the presence of a suitable catalyst such as palladium on carbon or palladium on barium sulfate. Basic hydrolysis of the ester with sodium hydroxide or potassium hydroxide followed by acid treatment gives a compound of formula 3 wherein W is hydrogen.

A compound represented by formula 3 wherein W is —CO$_2$R$_4$ and R$_4$ is hydrogen or a 1 to 4 carbon alkyl group may be prepared by reacting a corresponding compound wherein W is hydrogen with 2 to 3 equivalents of lithium diisopropylamine in a suitable solvent such as ethyl ether, propyl ether or tetrahydrofuran at −50° to 50° C. for from 1 to 2 hours. The dianion thus formed is reacted with a suitable carboxylating agent such as methyl chloroformate, ethyl chloroformate, propyl chloroformate, butyl chloroformate, dimethylcarbonate or diethylcarbonate at −70° to −50° C. for from 10 to 60 minutes and recovering the monoester of a substituted malonic acid and hydrolyzing the ester with a suitable base such as sodium hydroxide or potassium hydroxide, followed by treatment with a suitable acid such as hydrochloric, sulfuric or phosphoric to give the substituted malonic acid.

A compound represented by formula 3 wherein W is —SO$_3$R$_4$ and R$_4$ is hydrogen or a 1 to 4 carbon alkyl group may be prepared by reacting the corresponding compound wherein W is hydrogen with 1 to 2 equivalents of the dioxane-sulfur trioxide reagent in a suitable solvent such as methylene chloride, chloroform, carbon tetrachloride, ethylene dichloride or tetrachloroethane at a temperature of 0° to 30° C. for from 10 to 18 hours wherein the α-sulfo(2,3-dihydro-5-benzofuranyl)acetic acid is obtained. The thus obtained acid is treated with 2 to 3 equivalents of a suitable reagent such as, for example, the bromide or chloride, of phosphorus pentahalide, phosphorus trihalide, phosphorus oxyhalide or thionyl halide in a suitable solvent such as ethyl ether, methylene chloride, chloroform or carbon tetrachloride or benzene at from 20° C. to the boiling point of the solution for from 0.5 to 6 hours to form the diacid halide; reacting the thus formed diacid chloride with 1 equivalent of water at 10° to 30° C. for from 0.5 to 4 hours in a suitable solvent such as ethyl ether, methylene chloride, chloroform, carbon tetrachloride or benzene and reacting the thus formed chlorosulfonyl acetic acid derivative with a 1 to 4 carbon alcohol such as methanol, ethanol, propanol or butanol, optionally in the presence of a solvent such as ethyl ether or methylene chloride, and optionally in the presence of an acid acceptor such as triethylamine, sodium bicarbonate or potassium carbonate at 10° to 80° C. for from 0.5 hour to 6 hours to form the ester corresponding to the alcohol employed of the α-(alkoxysulfonyl)(2,3-dihydro-5-benzofuranyl)acetic acid.

The compounds of formula 3 wherein W is as described in formula 1 and optical isomers thereof are part of this invention. These compounds are useful as intermediates in the synthesis of the penicillin derivatives. The penicillin derivatives are useful as antibacterial agents.

The resolving agent used to separate the optically active isomers of D,L-α-amino(2,3-dihydro-5-benzofuranyl)acetic acid is binaphthylphosphoric acid (BPA), formula 4, the structure of which is shown below.

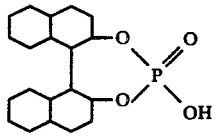

Formula 4

This material is fully described in *Tetrahedron Letters*, (1971), 4617. The acid used in this invention is (+)-BPA.

For the resolution, about 2 to 3 equivalents of the compound of formula 3, W is —NHR$_3$ (R$_3$=H), 1 to 2 equivalents of (+)-BPA and 1 to 3 equivalents of hydrogen chloride are reacted in methanol. The salt formed between the (+)-BPA and D-α-amino(2,3-dihydro-5-benzofuranyl)-acetic acid is separated and is reacted with equivalent amounts of sodium acetate trihydrate. D-α-Amino(2,3-dihydro-5-benzofuranyl)acetic acid is recovered as a solid.

The preferred compounds of this invention are the compounds of formula 1 wherein W is hydrogen, amino, hydroxyl, carboxyl and sulfo; R$_1$ is hydrogen and R$_2$ is hydrogen.

More preferred are those compounds of formula 1 when W is amino, R$_1$ is hydrogen and R$_2$ is hydrogen and the asymetric carbon of the 6-acetamido group is in the (D) configuration.

The daily dosage of the active ingredient may range from 1 mg to about 500 mg. The exact amount will vary with the patient's size, age and type of infection.

A typical tablet can have the following composition:

| | |
|---|---|
| 6-[[D-α-amino(2,3-dihydro-5-benzofuranyl)-acetyl]amino]-3,3-dimethyl-7-oxo-4-thia-1-azabicyclo[3.2.0]heptane-2-carboxylic acid | 125 mg |
| Lactose, USP | 250 mg |
| Cornstarch USP | 50 mg |
| Cornstarch, USP (as 10% starch paste) | 5 mg |
| Calcium Stearate | 2 mg |

The penicillin derivative, lactose and cornstarch are mixed and ground through a number 12 screen. The ground material is mixed with additional cornstarch as 10% starch paste and calcium stearate. Suitable size tablets can be prepared using a 5/16 inch diameter standard concave punch.

A typical parenteral solution may have the following composition:

| | |
|---|---|
| 6-[[D-α-amino(2,3-dihydro-5-benzofuranyl)-acetyl]amino]-3,3-dimethyl-7-oxo-4-thia-1-azabicyclo[3.2.0]heptane-2-carboxylic acid | 0.250 g |
| Sodium citrate | 0.006 g |
| Polyvinylpyrrolidone | 0.003 g |
| Lecithin | 0.010 g |
| Sodium carboxymethylcellulose | 0.003 g |
| Preservatives | |
|   Methylparaben | 0.09% |
|   Propylparaben | 0.01% |
| Sterile water to make | 1 cc |

Quantities required to make 1000 cc of parenteral solution, less the penicillin compound, are dissolved in about 250 cc of sterile water. The penicillin compound is added along with 100 cc of sterile water. The mixture is stirred and the final volume brought to 1000 cc by the addition of sterile water.

EXAMPLE 1

α-Amino(2,3-dihydro-5-benzofuranyl)acetic acid 2,3-Dihydrobenzofuran (4.8 g, 40 mmole) is stirred with 9.0 g (40 mmole) of α-hydroxyhippuric acid in 200 ml of 10% H$_2$SO$_4$-acetic acid mixture. The reaction is run at room temperature for 0.5 hour. After the half-hour, the reaction mixture is poured into 500 ml of water. The aqueous solution is extracted with ethyl acetate (4 × 100 ml). The ethyl acetate extracts are dried over magnesium sulfate and then evaporated to give α-benzamido(2,3-dihydro-5-benzofuranyl)acetic acid. Recrystallization of the crude benzamido compound from hexane-methylene chloride gives 11.56 g (94% yield).

The α-benzamido(2,3-dihydro-5-benzofuranyl)acetic acid (100 mg) is dissolved in 20 ml of methanol and 40 ml of water. Then 20 mg of Pd/C catalyst is added and the mixture subjected to 40 pounds/in$^2$ of hydrogen pressure for 4 hours. The mixture is filtered to remove the solid and the methanol is evaporated to give the title compound in about 60% yield.

NMR (DMSO-D$_6$)ppm(δ) 7.95(s,1); 6.7(m,3); 4.8(s,1); 4.42 (t,2); 2.95(t,2).

EXAMPLE 2

α-(tert-Butoxycarbonyl)amino(2,3-dihydro-5-benzofuranyl)acetic acid

α-Amino(2,3-dihydro-5-benzofuranyl)acetic acid (192 mg, 1 mmole) is added to 10 ml of 1:1 dioxane-water mixture with 4 mM of triethylamine and 0.17 or tertbutoxycarbonylazide. This mixture is stirred overnight at room temperature. The mixture is diluted with water and extracted with chloroform. The chloroform is dried and evaporated. The residue is taken up in ethyl acetate and washed with dilute aqueous hydrochloric acid. The organic layer is dried over magnesium sulfate and evaporated to give the title compound in a yield of about 80%.

NMR(CDCl$_3$)ppm(δ) 10.4(δ,1); 6.87(m,3); 5.5(broad, 1) 5.15(broad, 1); 4.6(t,2); 3.17(t,2); 1.35(s,9).

The identical procedure was used to prepare D-α-(tert-butoxycarbonyl)amino(2,3-dihydro-5-benzofuranyl)acetic acid from (D)-α-amino(2,3-dihydro-5-benzofuranyl)acetic acid.

EXAMPLE 3

α-Hydroxy(2,3-dihydro-5-benzofuranyl)acetic acid

α-Amino(2,3-dihydro-5-benzofuranyl)acetic acid (200 mg, 1.04 mmole) is dissolved in 250 mg (4.14 mmole) of glacial acetic acid and 145 mg (2.08 mmole) of sodium nitrite in about 5 ml of water is added dropwise. An additional 1 ml of glacial acetic acid is added and the mixture is heated to 65° C. and held at 65° C. for 4 hours. After cooling the reaction mixture is diluted with water and extracted with ethyl acetate for several hours. The ethyl acetate is dried over magnesium sulfate, filtered and evaporated to give about 65% of the title compound.

NMR(DMSO-D$_6$)ppm($\delta$)  7.15(m,3);  5.18(d,1); 4.78(t,2) and 3.34(t,2).

EXAMPLE 4

(2,3-Dihydro-5-benzofuranyl)acetic acid

α-Hydroxy(2,3-dihydro-5-benzofuranyl)acetic acid (10 mmole) is added to ethyl alcohol (20 ml) containing about 1 ml of concentrated sulfuric acid and the mixture heated (reflux) for 2 hours. Approximately half of the alcohol is removed, the remainder of the mixture is poured into about 160 ml of water. The aqueous mixture is extracted with chloroform, the chloroform is dried and the solvents are removed. The residue is used without further purification.

The ester prepared above (10 mmole) is added to about 25 ml of ether containing an acid acceptor such as triethylamine. Then acetyl chloride (0.01 mole) is slowly added to the ether solution which begins to reflux from the liberated heat. After stirring for 0.5 hours the solvents are removed and α-acetyloxy(2,3-dihydro-5-benzofuranyl)acetic acid ethyl ester is recovered as the residue.

The acetylated hydroxy ester (10 mmole) is dissolved in 40 ml of methanol to which is added about 50 mg of a palladium on carbon catalyst. The mixture is subjected to 40 pounds/in$^2$ of hydrogen pressure for 4 hours. At the end of this time the mixture is filtered to remove the catalyst and the solvent is removed. The residue, (2,3-dihydro-5-benzofuranyl)acetic acid, ethyl ester is dissolved in methanol and a 10% excess of sodium hydroxide is added. The mixture is refluxed for about 60 minutes and the solvent removed by evaporation. The residue is taken up in water and the pH adjusted to about 2. The title compound precipitates from solution and is recovered by filtration.

EXAMPLE 5

2-(2,3-Dihydro-5-benzofuranyl)malonic acid

To a solution of diisopropylamide (20 mmole) in 50 ml of anhydrous tetrahydrofuran (THF) maintained under a nitrogen atmosphere at −40° C. is added n-butyllithium (20 mmole). The mixture is stirred for 15 minutes and then (2,3-dihydro-5-benzofuranyl)acetic acid (10 mmole) is added. The mixture is heated at 50° C. for 1 hour and then cooled to −70° C. and ethyl chloroformate (10 mmole) is added. The temperature is increased and the mixture is stirred for about 20 minutes. The mixture is poured over ice and hydrochloric acid. The aqueous phase is extracted with ether. The ether extracts are combined, dried and evaporated to give 2-(2,3-dihydro-5-benzofuranyl)malonic acid, monoethyl ester.

The monoethyl ester of 2-(2,3-dihydro-5-benzofuranyl)malonic acid (10 mmole) is added to methanol containing 11 mmole of sodium hydroxide. The mixture is refluxed for about 30 minutes and then the methanol is removed. The residue is taken up in water. Adjustment of the pH to 2 with hydrochloric acid results in the precipitation of the title acid. The title acid is filtered and dried.

EXAMPLE 6

α-Sulfo(2,3-dihydro-5-benzofuranyl)acetic acid

The title compound is prepared by a modification of the procedure described in *J. Am. Chem. Soc.*, 75, 1653 (1953). To a solution of ethylene chloride is added about 15 mmole of the dioxane-sulfur trioxide reagent and the temperature of the mixture warms to room temperature. (2,3-Dihydro-5-benzofuranyl)acetic acid (10 mmole) is added over a period of 30 minutes. The solution is stirred overnight at room temperature and then poured into cold water. The organic layer is separated and extracted with water. The aqueous extracts are combined with the water layer which is neutralized with sodium hydroxide and evaporated to dryness. The residue is extracted with 70% ethanol. Concentrating the alcohol solution and subsequent cooling gives the sodium salt of α-sulfo(2,3-dihydro-5-benzofuranyl)acetic acid. Treatment of the sodium salt with hydrochloric acid followed by recrystallization of the acid from ethanol gives the title compound.

EXAMPLE 7

(D)-α-Amino(2,3-dihydro-5-benzofuranyl)acetic acid

The resolving agent, binaphthyl phosphoric acid (BPA), is described in *Tetrahedron Letters*, 1971, 4617.

A racemic mixture of D,L-α-amino(2,3-dihydro-5-benzofuranyl)acetic acid is prepared according to the procedure in Example 2. The racemic mixture, 2.7 g (13.99 mmole), is treated with 3.5 g (10 mmole of (+)−binaphthyl phosphoric acid (BPA) and 4 mmole of hydrochloric acid in 25 ml of methanol. This mixture is refluxed for 30 minutes. After cooling to 0° C., the salt formed between (+)−BPA and D-α-amino(2,3-dihydro-5-benzofuranyl)acetic acid precipitates and is filtered. A total of 2.76 g (51%) of salt is obtained.

The (+) BPA-D-α-amino(2,3-dihydro-5-benzofuranyl)acetic acid salt (2.76 g, 5.1 mmole) is slurried in 50 ml of methanol. Sodium acetate trihydrate (0.691 g, 5.1 m mole) is added and the mixture is refluxed for 1 hour. The hot solution is filtered and the solid is washed with hot methanol to give 0.88 g (90% of D-α-amino(2,3-dihydro-5-benzofuranyl)acetic acid, $[\alpha]_D^{20}$ = −131°.

EXAMPLE 8

D-α-(3-Ethoxy-1-methyl-3-oxo-1-propen-1-yl)amino-2,3-dihydro-5-benzofuranacetic acid D-α-Amino(2,3-dihydro-5-benzofuranyl)acetic acid (35 mmole) in 40 ml of 1 N methanolic potassium hydroxide is mixed with a solution of the ethyl ester of acetoacetic acid (38 mmole) in 20 ml of methanol. This mixture is heated to boiling for 10 minutes. The solution is cooled to precipitate and product. The precipitated material is filtered and recrystallized from absolute ethanol to give the title compound.

EXAMPLE 9

D-α-(N-Benzoyloxycarbonyl)amino(2,3-dihydro-5-benzofuranyl)acetic acid

D-α-Amino(2,3-dihydro-5-benzofuranyl)acetic acid (50 mmole) is dissolved in 150 ml of 1 N sodium hydroxide. This mixture is cooled to 0° C. and over a period of 45 minutes about 52 mmole of benzoyloxychloroformate and 1 N sodium hydroxide is added. Only enough sodium hydroxide is added so as to maintain the pH of the reaction mixture at about 8 to 9. After the addition is complete the mixture is stirred for 30 minutes at 0° C. and for an additional 30 minutes while the mixture warms to room temperature. The basic reaction mixture is washed with ether, is cooled to 0° C. and is added to ice cold 5 N hydrochloric acid. The title compound is recovered from the hydrochloric acid solution.

EXAMPLE 10

6-[[D-α-Amino(2,3-dihydro-5-benzofuranyl)acetyl]amino]-3,3-dimethyl-7-oxo-4-thia-1-azabicyclo[3.2.0]heptane-2-carboxylic acid A solution of 250 mg (1.16 mmole) of 6-amino-3,3-dimethyl-7-oxo-4-thia-1-azabicyclo[3.2.0]heptane-2-carboxylic acid (6-APA) in 3 ml of water containing 150 mg (1.5 mmole) of triethylamine and 1 ml of acetone is prepared and chilled in an ice bath. Then 400 mg (1.17 mmole) of D-α-(3-ethoxy-1-methyl-3-oxo-1-propen-1-ylamino)-2,3-dihydro-5-benzofuranacetic acid (Dane's salt) is suspended in 5 ml of anhydrous acetone and 1 drop of N-methylmorpholine. Ethylchloroformate (125 mg, 1.16 mmole) in 2 ml of acetone is added to the solution of Dane's salt which is maintained at about −15° C. This mixture is stirred an additional 30 minutes, the temperature is reduced from −15° C. to −30° C. and the solution containing the 6-APA is added in one portion. The resulting mixture of Dane's salt and 6-APA is stirred for 1 hour at −10° C. and then allowed to warm to 20° C. from −10° C. The pH is adjusted to 2 with hydrochloric acid. Ether is then used to extract the aqueous mixture so as to remove the hydrolyzed protecting group from the aqueous solution. The pH is then adjusted to 5 by the addition of triethylamine. The aqueous solution is stored at about 0° C. for a period of about 50 hours (over the weekend). A solid precipitates which is washed with water. A yield of 40% of a white solid (the title compound) is obtained.

In like manner and using appropriate quantities of 6-amino-3,3-dimethyl-7-oxo-4-thia-1-azabicyclo[3.2.0]heptane-2-carboxylic acid, ethyl ester in place of 6-amino-3,3-dimethyl-7-oxo-4-thia-1-azabicyclo[3.2.0]heptane-2-carboxylic acid gives 6-[[D-α-amino(2,3-dihydro-5-benzofuranyl)acetyl]amino]-3,3-dimethyl-7-oxo-4-thia-1-azabicyclo[3.2.0]heptane-2-carboxylic acid, ethyl ester.

EXAMPLE 11

6-[[(2,3-Dihydro-5-benzofuranyl)hydroxyacetyl]amino]-3,3-dimethyl-7-oxo-4-thia-1-azabicyclo[3.2.0]heptane-2-carboxylic acid (2,3-Dihydro-5-benzofuranyl)hydroxyacetic acid (10 mmole), triethylamine (10 mmole) and bistrimethylsilylacetamide (BSA) (10 mmole) are added to 50 ml of tetrahydrofuran and refluxed for 2 hours. The reaction mixture is cooled to about −10° C. and 10 mmole of isobutylchloroformate is added dropwise. After 30 minutes at −10° C., 10 mmole of 6-amino-3,3-dimethyl-7-oxo-4-thia-1-azabicyclo[3.2.0]heptane-2-carboxylic acid in 50 ml of water-20 ml of tetrahydrofuran containing 10 mmole of triethylamine is added dropwise to the previously prepared solution which is at about −10° C. After the addition is complete, the temperature is allowed to rise to room temperature from −10° C. About 50 ml of saturated sodium bicarbonate and 100 ml of water are added to the reaction mixture which is then twice extracted with ether. The aqueous phase is layered with ethyl acetate and the pH is adjusted to 1.5 by the addition of hydrochloric acid. The ethyl acetate is separated from the aqueous phase, dried over magnesium sulfate, filtered and evaporated to give the title compound.

In like manner and using equivalent amounts of 6-amino-3,3-dimethyl-7-oxo-4-thia-1-azabicyclo[3.2.0]heptane-2-carboxylic acid, ethyl ester and 6-amino-3,3-dimethyl-7-oxo-4-thia-1-azabicyclo[3.2.0]heptane-2-carboxylic acid, p-(acetyloxy)benzyl ester in place of 6-amino-3,3-dimethyl-7-oxo-4-thia-1-azabicyclo[3.2.0]heptane-2-carboxylic acid gives the respective compounds: 6-[[(2,3-Dihydro-5-benzofuranyl)hydroxyacetyl]amino]3,3-dimethyl-7-oxo-4-thia-1-azabicyclo[3.2.0]heptane-2-carboxylic acid, ethyl ester; and 6-[[(2,3-dihydro-5-benzofuranyl)hydroxyacetyl]amino]-3,3-dimethyl-7-oxo-4-thia-1-azabicyclo[3.2.0]heptane-2-carboxylic acid, p-(acetyloxy)benzyl ester.

EXAMPLE 12

6-[[Carboxy(2,3-dihydro-5-benzofuranyl)acetyl]amino]-3,3-dimethyl-7-oxo-4-thia-1-azabicyclo[3.2.0]heptane-2-carboxylic acid The title compound is prepared according to the general procedure (EXAMPLE 3) described in U.S. Pat. No. 3,282,926.

α-Carboxy(2,3-dihydro-5-benzofuranyl)acetic acid (14 mmole) is added to 50 ml of ether. Thionyl chloride (14.5 mmole) is added along with 1 drop of dimethylformamide. This mixture is refluxed about 3 hours and then evaporated under reduced pressure at room temperature. The residue is added to 50 ml of ether which is added to an ice cold mixture of 6-amino-3,3-dimethyl-7-oxo-4-thia-1-azabicyclo[3.2.0]heptane-2-carboxylic acid (14 mmole), 30 ml of water, 15 ml of ether and triethylamine (14 mmole). After stirring for 30 minutes the pH is adjusted to 1.5 with dilute hydrochloric acid and the layers separated. The ether layer is extracted with water. Evaporation of the ether gives a residue which is taken up in ethyl acetate, dried, filtered and evaporated to give the title compound.

In like manner and using equivalent amounts of α-carbethoxy(2,3-dihydro-5-benzofuranyl)acetic acid and α-sulfo(2,3-dihydro-5-benzofuranyl)acetic acid in place of α-carboxy)2,3-dihydro-5-benzofuranyl)acetic acid gives 6-[[carbethoxy(2,3-dihydro-5-benzofuranyl)acetyl]amino]-3,3-dimethyl-7-oxo-4-thia-1-azabicyclo[3.2.0]-heptane-2-carboxylic acid and 6-[[sulfo(2,3-dihydro-5-benzofuranyl)acetyl]amino]-3,3-dimethyl-7-oxo-4-thia-1-azabicyclo[3.2.0]heptane-2-carboxylic acid.

EXAMPLE 13

6-[[Sulfo(2,3-dihydro-5-benzofuranyl)acetyl]amino]-3,3-dimethyl-7-oxo-4-thia-1-azabicyclo[3.2.0]heptane-2-carboxylic acid Sulfo(2,3-dihydro-5-benzofuranyl)acetyl chloride is prepared according to the general procedure described in *J. Med. Chem.*, 15, 1105 (1972). Sulfo(2,3-dihydro-5-benzofuranyl)acetic acid (20 mmole) is added slowly to a solution of ether (4 ml) and thionyl chloride (150 mmole). The mixture is stirred at room temperature until the gas evolution stopped. Then about 0.2 ml of dimethylformamide is added and the solution heated at 40° C. for 4 hours. The mixture is diluted with 30 ml of ether and 30 ml of hexane and then cooled to −25° C. Sulfo(2,3-dihydro-5-benzofuranyl)acetyl chloride is recovered from the mixture and used without further purification.

Sulfo(2,3-dihydro-5-benzofuranyl)acetyl chloride (5 mmole) in 10 ml of ether is added to 5 mmole of 6-amino-3,3-dimethyl-7-oxo-4-thia-1-azabicyclo[3.2.0]heptane-2-carboxylic acid dissolved in 10 ml of water containing 10 mmole of sodium bicarbonate. The temperature is maintained at about 0° C. during the addition. The reaction mixture is stirred for about 30 minutes at 0° C. The organic phase is separated from the aqueous phase. The pH of the aqueous phase is adjusted to 6.5 to 7.0. The aqueous phase is extracted with ethyl acetate. The ethyl acetate is dried over magnesium sulfate, filtered and evaporated to give the title compound.

In like manner and using equivalent quantities of 6-amino-3,3-dimethyl-7-oxo-4-thia-1-azabicyclo[3.2.0]heptane-2-carboxylic acid, ethyl ester in place of 6-amino-3,3-dimethyl-7-oxo-4-thia-1-azabicyclo[3.2.0]heptane-2-carboxylic acid gives 6-[[sulfo(2,3-dihydro-5-benzofuranyl)acetyl]amino]-3,3-dimethyl-7-oxo-4-thia-1-azabicyclo[3.2.0]heptane-2-carboxylic acid, ethyl ester.

EXAMPLE 14

6-[[D-α-(3-Ethoxy-1-methyl-3-oxo-1-propen-1-yl)amino(2,3-dihydro-5-benzofuranyl)acetyl]amino]-3,3-dimethyl-7-oxo-4-thia-1-azabicyclo[3.2.0]heptane-2-carboxylic acid, triethylamine salt A solution of 250 mg (1.16 mmole) of 6-amino-3,3-dimethyl-7-oxo-4-thia-1-azabicyclo[3.2.0]heptane-2-carboxylic acid (6-APA) in 3 ml of water containing 150 mg (1.5 mmole) of triethylamine and 1 ml of acetone is prepared and chilled in an ice bath. Then 400 mg (1.17 mmole of D-α-(3-ethoxy-1-methyl-3-oxo-1-propen-1-ylamino)-2,3-dihydro-5-benzofuranacetic acid (Dane's salt) is suspended in 5 ml of anhydrous acetone and 1 drop of N-methylmorpholine. Ethylchloroformate (125 mg, 1.16 mmole) in 2 ml of acetone is added to the solution of Dane's salt which is maintained at about −15° C. This mixture is stirred an additional 30 minutes, the temperature is reduced from −15° C. to −30° C. and the solution containing the 6-APA is added in one portion. The resulting mixture of Dane's salt and 6-APA is stirred for 1 hour at −10° C. and then allowed to warm to room temperature from −10° C. The solvents, water and acetone, are removed under reduced pressure while maintaining the temperature of the mixture at about 10°-15° C. The solid, which is the title compound, is used without further purification.

In a similar manner and using an equivalent amount of 6-amino-6-methoxy-3,3-dimethyl-7-oxo-4-thia-1-azabicyclo[3.2.0]heptane-2-carboxylic acid in place of 6-amino-3,3-dimethyl-7-oxo-4-thia-1-azabicyclo[3.2.0]heptane-2-carboxylic acid gives 6-[[D-α-(3-ethoxy-1-methyl-3-oxo-1-propen-1-yl)amino(2,3-dihydro-5-benzofuranyl)acetyl]amino]-3,3-dimethyl-7-oxo-4-thia-1-azabicyclo-[3.2.0]heptane-2-carboxylic acid, triethylamine salt.

EXAMPLE 15

6-[[D-α-Amino(2,3-dihydro-5-benzofuranyl)acetyl]amino]-3,3-dimethyl-7-oxo-4-thia-1-azabicyclo[3.2.0]heptane-2 carboxylic acid, ethyl ester 6-[[D-α-(3-Ethoxy-1-methyl-3-oxo-1-propen-1-yl)amino-(2,3-dihydro-5-benzofuranyl)acetyl]amino]-3,3-dimethyl-7-oxo-4-thia-1-azabicyclo[3.2.0]heptane-2-carboxylic acid, triethylamine salt, hereinafter referred to as Penicillin Compound A, (5 mmole) is added to 25 ml of dimethylformamide. This mixture is stirred for 30 minutes at 20° C. after which ethyl bromide (5.5 mmole) is added. Stirring is continued for 2 to 3 hours followed by dilution with ethyl acetate and water. The pH is adjusted to about 2 by the addition of hydrochloric acid. The mixture is extracted with ethyl ether to remove the hydrolyzed protecting group. The pH is adjusted to 6.5–7.0 by the addition of triethylamine or aqueous sodium bicarbonate. Ethyl acetate is added, is thoroughly mixed with the aqueous solution, is separated and washed with water, dried and evaporated to give the title compound.

Using this procedure, the compounds listed in the table are prepared.

| Penicillin Compound | Halide | Product |
| --- | --- | --- |
| Penicillin Compound A | tert-Butylchloride | 6-[[D-α-Amino(2,3-dihydro-5-benzofuranyl)acetyl]amino]-3,3-dimethyl-7-oxo-4-thia-1-azabicyclo[3.2.0]heptane-2-carboxylic acid, tert butyl ester |
| Penicillin Compound A | Chloromethylacetate | 6-[[-α-Amino(2,3-dihydro-5-benzofuranyl)acetyl]amino]-3,3-dimethyl-7-oxo-4-thia-1-axabicyclo[3.2.0]heptane-2-carboxylic acid acetyloxy methyl ester |
| Penicillin Compound A | Chloromethylpivalate | 6-[[D-α-Amino(2,3-dihydro-5-benzofuranyl)acetyl]amino]-3,3-dimethyl-7-oxo-4-thia-1-azabicyclo[3.2.0]heptane-2-carboxylic acid, pivaloyloxymethyl ester |
| Penicillin Compound A | N-butyrylaminomethyl chloride | 6-[[D-α-Amino(2,3-dihydro-5-benzofuranyl)acetyl]amino]-3,3-dimethyl-7-oxo-4-thia-1-azabicyclo[3.2.0]heptane-2-carboxylic acid, N-butyrylaminomethyl ester |
| Penicillin Compound A | N-methyl-N-butyrylaminomethyl | 6[[D-α-Amino(2,3-dihydro-5-benzofuranyl)acetyl]amino]-3,3-dimethyl-7-oxo-4-thia-1-azabicyclo[3.2.0]heptane-2-carboxylic acid, N-methyl-N-butyrylamino- |

| Penicillin Compound | Halide | Product |
|---|---|---|
| | | methyl ester |

EXAMPLE 16

6-Amino-3,3-dimethyl-7-oxo-4-thia-1-azabicyclo[3.2.0]heptane-2-carboxylic acid, ethyl ester 6-Amino-3,3-dimethyl-7-oxo-4-thia-1-azabicyclo[3.2.0]heptane-2-carboxylic acid, sodium salt, hereinafter referred to as 6-APA, sodium salt, (5.0 mmole) is added to 50 ml of dimethylformamide at room temperature. After stirring for 15 minutes, 5.5 mmole of ethyl bromide is added. This mixture is stirred for 2 to 3 hours after which it is diluted with ethyl acetate and water. The pH is adjusted to about 6.5 to 7.0 by the addition of hydrochloric acid and the organic phase is separated from the aqueous phase. The organic phase is washed with water, dried over magnesium sulfate, filtered and evaporated to give the title compound.

Using this procedure, the compounds listed in the table are prepared.

| Penicillin Compound | Halide | Product |
|---|---|---|
| 6-APA, sodium salt | n-butylbromide | 6-Amino-3,3-dimethyl-7-oxo-4-thia-1-azabicyclo[3.2.0]heptane-2-carboxylic acid, n-butyl ester |
| 6-APA, sodium salt | tert-butyl chloride | 6-Amino-3,3-dimethyl-7-oxo-4-thia-1-azabicyclo[3.2.0]heptane-2-carboxylic acid, tert-butyl ester |
| 6-APA, sodium salt | chloromethylpropionate | 6-Amino-3,3-dimethyl-7-oxo-4-thia-1-azabicyclo[3.2.0]heptane-2-carboxylic acid, propionyloxymethyl ester |
| 6-APA, sodium salt | N-acetylaminomethyl chloride | 6-Amino-3,3-dimethyl-7-oxo-4-thia-1-azabicyclo[3.2.0]heptane-2-carboxylic acid, N-acetylaminomethyl ester |
| 6-Amino-6-methoxy-3,3-dimethyl-7-oxo-4-thia-1-azabicyclo-[3.2.0]heptane-2-carboxylic acid, sodium salt | chloromethypivalate | 6-Amino-6-methoxy-3,3-dimethyl-7-oxo-4-thia-1-azabicyclo-[3.2.0]heptane-2-carboxylic acid, pivaloyloxymethyl ester |

EXAMPLE 17

6-Amino-3,3-dimethyl-7-oxo-4-thia-1-azabicyclo[3.2.0]heptane-2-carboxylic acid, p-(acetyloxy)benzyl ester 6-Amino-3,3-dimethyl-7-oxo-4-thia-1-azabicyclo[3.2.0]heptane-2-carboxylic acid, sodium salt (5 mmole) in 50 ml of dimethylformamide is stirred at room temperature while 2 equivalents of p-(acetyloxy)benzyl alcohol is added. The mixture is cooled to 0° C. after which 5.5 mmole of dicyclohexylcarbodiimide in 10 ml of dimethylformamide is added. This mixture is stirred at 0° C. for 1 hour and at room temperature for 4 hours. Dicyclohexylurea is removed by filtration. The filtrate is diluted with chloroform, washed with water, dried over magnesium sulfate, filtered and evaporated to give the title compound.

In like manner and using equivalent amounts of p-(propionyloxy)benzyl alcohol, p-(pivaloxyloxy)benzyl alcohol and p-(butyryloxy)benzyl alcohol in place of p-(acetyloxy)benzyl alcohol gives the following respective compounds:
6-Amino-3,3-dimethyl-7-oxo-4-thia-1-azabicyclo[3.2.0]heptane-2-carboxylic acid, p-(propionyloxy)benzyl ester; 6-Amino-3,3-dimethyl-7-oxo-4-thia-1-azabicyclo[3.2.0]heptane-2-carboxylic acid, p-(pivaloyloxy)benzyl ester; and 6-Amino-3,3-dimethyl-7-oxo-4-thia-1-azabicyclo[3.2.0]heptane-2-carboxylic acid, p-(butyryloxy)benzyl ester.

EXAMPLE 18

6-[[Ethoxysulfonyl(2,3-dihydro-5-benzofuranyl)]acetyl]amino-3,3-dimethyl-7-oxo-4-thia-1-azabicyclo[3.2.0]heptane-2-carboxylic acid α-Sulfo(2,3-dihydro-5-benzofuranyl)acetic acid, as prepared in Example 6, (5 mmole) is added to 50 ml of ether and 55 mmole of thionyl chloride and 0.3 ml of dimethylformamide. This mixture is stirred at 20° C. for 50 hours. At the end of this time the ether and the excess thionyl chloride are removed. The dichloride crystallizes after it is cooled overnight. Then 5 mmole of the dichloride is added to 50 ml of anhydrous ether. Then 10 ml of ether containing 5 mmole of water is added and the mixture stirred. The hydrolysis being complete, the solvent is removed along with the hydrogen chloride liberated. The residue is chlorosulfonyl(2,3-dihydro-5-benzofuranyl)acetic acid.

α-Chlorosulfonyl(2,3-dihydro-5-benzofuranyl)acetic acid (5 mmole) is added to 30 ml of ethyl acetate. To this mixture is added 5 mmole of ethanol in 10 ml of ethyl acetate which contains 10 mmole of triethylamine. The mixture is stirred at room temperature for about 1 hour and 50 ml of water is added. The pH is adjusted to about 6.5 and the layers separated. The organic layer is dried over magnesium sulfate, filtered and evaporated to give ethoxysulfonyl(2,3-dihydro-5-benzofuranyl)acetic acid.

Ethoxysulfonyl(2,3-dihydro-5-benzofuranyl)acetic acid (5 mmole) in 50 ml of dry ether is reacted with about 5.5 mmole of thionyl chloride at 20° C. for 4 hours. At the end of this time the solvent is removed to insure that all of the thionyl chloride and hydrochloric acid is removed. It is then redissolved in 10 ml of ether. This ether solution is added to 10 ml of water containing 5 mmole of 6-amino-3,3-dimethyl-7-oxo-4-thia-1-azabicyclo[3.2.0]heptane-2-carboxylic acid and 10 mmole of sodium bicarbonate. The temperature of the aqueous solution is about 10° C. After stirring for about 2 hours, the pH is adjusted to about 2. Ethyl acetate is added, the mixture is thoroughly agitated and the layers separated. The organic layer is dried over magnesium sulfate, filtered and evaporated to give the title compound.

In like manner and using the appropriate amount of 6-amino-3,3-dimethyl-7-oxo-4-thia-1-azabicyclo[3.2.0]heptane-2-carboxylic acid, tert-butyl ester in place of 6-amino-3,3-dimethyl-7-oxo-4-thia-1-azabicyclo[3.2.0]heptane-2-carboxylic acid gives 6-[[ethoxysulfonyl(2,3-dihydro-5-benzofuranyl)acetyl]amino]-3,3-dimethyl-7-oxo-4-thia-1-azabicyclo[3.2.0]heptane-2-carboxylic acid, tert-butyl ester.

EXAMPLE 19

α-Acetamido(2,3-dihydro-5-benzofuranyl)acetic acid

α-Amino(2,3-dihydro-5-benzofuranyl)acetic acid (10 mmole) is dissolved in 25 ml of water containing 20 mmole of sodium hydroxide. The temperature is maintained at 10° C. while 10.5 mmole of acetyl chloride in 10 ml of ether is added over a period of 10 minutes. The reaction mixture is stirred for 20 minutes. Ethyl acetate is added and the pH is adjusted to 2 with hydrochloric acid. The layers are separated, the organic layer is dried over magnesium sulfate, filtered and evaporated to give the title compound.

EXAMPLE 20

α-[[(Acetyloxy)methoxy]carbonyl]-(2,3-dihydro-5-benzofuranyl)acetic acid

α-Carboxy(2,3-dihydro-5-benzofuranyl)acetic acid (10 mmole) is dissolved in 50 ml of water containing 10 mmole of sodium hydroxide. This mixture is stirred for 30 minutes at room temperature and then 10 mmole of chloromethylacetate in 25 ml of ether is added. The temperature during the addition is 10° C.; after the addition is complete, the temperature is raised to 20° C. and the mixture stirred for an additional 30 minutes. The pH is adjusted to 2 and ethyl acetate is added. The organic phase is removed, dried over magnesium sulfate, filtered and evaporated to give the title compound.

In a similar manner and using an equivalent amount of α-sulfo(2,3-dihydro-5-benzofuranyl)acetic acid for α-carboxy(2,3-dihydro-5-benzofuranyl)acetic acid gives α-[[(acetyloxy)methoxy]sulfonyl]-(2,3-dihydro-5-benzofuranyl)acetic acid.

I claim:

1. A compound selected from the formula

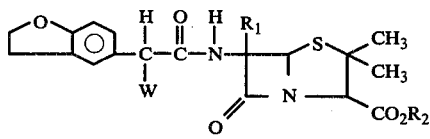

wherein W is hydrogen, $-NHR_3$, $-OH$, $-CO_2R_4$ or $-SO_3R_4$ wherein $R_3$ is hydrogen, a straight or branched 2 to 5 carbon alkanoyl group, an alkoxycarbonyl group in which the alkoxy group is straight or branched and contains 1 to 4 carbon atoms; $R_4$ is hydrogen, a straight or branched 1 to 4 carbon alkyl group; $R_1$ is hydrogen or methoxy; $R_2$ is hydrogen, a straight or branched alkyl group of from 1 to 4 carbon atoms, an alkanoyloxymethyl group in which the alkanoyl moiety is straight or branched and has from 2 to 5 carbon atoms, an alkanoylaminomethyl group wherein the alkanoyl moiety is straight or branched and has from 2 to 5 carbon atoms and the amino nitrogen may be substituted with a straight or branched alkyl group of from 1 to 4 carbon atoms, a p-(alkanoyloxy)benzyl group in which the alkanoyl moiety has from 2 to 5 carbon atoms and is straight or branched, or an aminoalkanoyloxymethyl group wherein the alkanoyl moiety is straight or branched and contains from 2 to 15 carbon atoms and the amino nitrogen may be mono- or disubstituted with a straight or branched alkyl group of from 1 to 4 carbon atoms; and non-toxic pharmaceutically acceptable salts and individual optical isomers thereof.

2. A compound of claim 1 wherein $R_1$ is hydrogen.

3. A compound of claim 2 wherein W is hydrogen.

4. A compound of claim 2 wherein W is $-NHR_3$ wherein $R_3$ is hydrogen.

5. A compound of claim 2 wherein W is $-OH$.

6. A compound of claim 2 wherein W is $-COOR_4$ wherein $R_4$ is hydrogen.

7. A compound of claim 2 wherein W is $-SO_3R_4$ wherein $R_4$ is hydrogen.

8. A compound of claim 1 which is 6-[[D-α-amino(2,3-dihydro-5-benzofuranyl)acetyl]amino]-3,3-dimethyl-7-oxo-4-thia-1-azabicyclo[3.2.0]heptane-2-carboxylic acid or a pharmaceutically acceptable salt thereof.

9. A compound of claim 1 which is 6-[[(2,3-dihydro-5-benzofuranyl)hydroxyacetyl]amino]-3,3-dimethyl-7-oxo-4-thia-1-azabicyclo[3.2.0]heptane-2-carboxylic acid or a pharmaceutically acceptable salt thereof.

10. A compound of claim 1 which is 6-[[(carboxy(2,3-dihydro-5-benzofuranyl)acetyl]amino]-3,3-dimethyl-7-oxo-4-thia-1-azabicyclo[3.2.0]heptane-2-carboxylic acid or a pharmaceutically acceptable salt thereof.

11. A compound of claim 1 which is 6-[[(2,3-dihydro-5-benzofuranyl)sulfoacetyl]amino]-3,3-dimethyl-7-oxo-4-thia-1-azabicyclo[3.2.0]heptane-2-carboxylic acid or a pharmaceutically acceptable salt thereof.

12. A compound of claim 1 which is 6-[[(2,3-dihydro-5-benzofuranyl)acetyl]amino]-3,3-dimethyl-7-oxo-4-thia-1-azabicyclo[3.2.0]heptane-2-carboxylic acid or a pharmaceutically acceptable salt thereof.

* * * * *